United States Patent
Wdowin (10) Patent No.: US 11,304,894 B2
(45) Date of Patent: Apr. 19, 2022

(54) COMPOSITIONS, DELIVERY DEVICES, AND METHODS THEREOF FOR FEMININE HEALTH

(71) Applicant: Garrett E. Wdowin, Corona Del Mar, CA (US)

(72) Inventor: Garrett E. Wdowin, Corona Del Mar, CA (US)

( * ) Notice: Subject to any disclaimer, the term of this patent is extended or adjusted under 35 U.S.C. 154(b) by 0 days.

(21) Appl. No.: 16/866,454

(22) Filed: May 4, 2020

(65) Prior Publication Data

US 2021/0338572 A1   Nov. 4, 2021

(51) Int. Cl.

| | |
|---|---|
| *A61K 9/00* | (2006.01) |
| *A61K 36/30* | (2006.01) |
| *A61F 13/472* | (2006.01) |
| *A61K 9/70* | (2006.01) |
| *A61K 33/06* | (2006.01) |
| *A61K 31/675* | (2006.01) |
| *A61K 31/519* | (2006.01) |
| *A61K 33/22* | (2006.01) |
| *A61K 47/02* | (2006.01) |
| *A61K 31/07* | (2006.01) |
| *A61K 31/355* | (2006.01) |
| *A61K 35/747* | (2015.01) |
| *A61K 36/888* | (2006.01) |
| *A61K 36/886* | (2006.01) |
| *A61K 36/63* | (2006.01) |
| *A61K 36/14* | (2006.01) |
| *A61K 36/61* | (2006.01) |
| *A61F 13/20* | (2006.01) |

(52) U.S. Cl.
CPC ........ *A61K 9/0036* (2013.01); *A61F 13/2074* (2013.01); *A61F 13/472* (2013.01); *A61K 9/7007* (2013.01); *A61K 31/07* (2013.01); *A61K 31/355* (2013.01); *A61K 31/519* (2013.01); *A61K 31/675* (2013.01); *A61K 33/06* (2013.01); *A61K 33/22* (2013.01); *A61K 35/747* (2013.01); *A61K 36/14* (2013.01); *A61K 36/30* (2013.01); *A61K 36/61* (2013.01); *A61K 36/63* (2013.01); *A61K 36/886* (2013.01); *A61K 36/888* (2013.01); *A61K 47/02* (2013.01)

(58) Field of Classification Search
CPC .... A61K 9/0036; A61K 36/30; A61K 9/7007; A61K 33/06; A61K 31/675; A61K 31/519; A61K 33/22; A61K 47/02; A61K 31/07; A61K 31/355; A61K 35/747; A61K 36/888; A61K 36/868; A61K 36/63; A61K 36/14; A61K 36/61; A61F 13/472; A61F 13/2074
See application file for complete search history.

(56) References Cited

U.S. PATENT DOCUMENTS

| | | | |
|---|---|---|---|
| 3,905,372 A | * | 9/1975 | Denkinger .......... A61F 13/2051 604/359 |
| 6,284,261 B1 | | 9/2001 | Tramontana |
| 7,341,737 B2 | | 3/2008 | Gehling et al. |
| 8,288,142 B2 | | 10/2012 | Uvarkina et al. |
| 2014/0356424 A1 | * | 12/2014 | Vilar ..................... A61K 33/04 424/456 |
| 2015/0071978 A1 | | 3/2015 | Chang |
| 2018/0235987 A1 | * | 8/2018 | von Maltzahn ......... A61K 8/60 |

FOREIGN PATENT DOCUMENTS

| | | | |
|---|---|---|---|
| CN | 104661628 | * | 5/2015 |
| CN | 107847768 | * | 3/2018 |
| EP | 1467705 | * | 6/2012 |
| WO | 2007142609 A2 | | 12/2007 |
| WO | WO 2014/101049 | * | 7/2014 |

OTHER PUBLICATIONS

Koenig et al. (WO 2014/101049) and Smeets et al. (CN 107847768).*
"10 pack Chinese Herbal Tampon for Women (Clean Point Tampon) for sale online" https://www.ebay.com/c/935681209 last accessed Aug. 5, 2020.
"Vaginal Dryness" https://siteman.wustl.edu/treatment/survivorship/vaginal-dryness/ last accessed Aug. 5, 2020.
Ajayraj N. Chudasama "Vaginal Drug Delivery Systems" http://www.authorstream.com/Presentation/AJ07-1177391-vaginal-drug-delivery-system/ published Sep. 7, 2011.
Borges et al. "The role of lactobacilli and probiotics in maintaining vaginal health." Arch Gynecol Obstet (2014) 289:479-489 published Oct. 30, 2013.
Chatterjee et al. "An Overview of Intra-Vaginal Drug Delivery System" Journal of Pharmacy Research 2009, 2(4) 698-700 published Apr. 2, 2009.
Clagett-Dame et al. "Vitamin A in Reproduction and Development." Nutrients 2011, 3, 385-428 published Mar. 29, 2011.

(Continued)

*Primary Examiner* — Shirley V Gembeh
(74) *Attorney, Agent, or Firm* — Rutan & Tucker LLP (57) ABSTRACT

Disclosed herein are compositions, delivery devices and methods for feminine health. A delivery device for feminine health can include a feminine hygiene product including an absorbent substrate and a composition absorbed onto the absorbent substrate for placement against a vulva, inserted into a vagina, or both. The composition can include a continuous phase and a dispersed phase dispersed throughout the continuous phase forming a fluid suspension. The continuous phase can include a solvent of one or more essential oils, one or more lubricants, or a combination thereof. The continuous phase can include one or more solutes dissolved in the solvent including one or more fat-soluble vitamins. The dispersed phase can include a pH-balancing agent, a dietary mineral, an absorbent, one or more water-soluble vitamins, or a combination thereof.

16 Claims, 5 Drawing Sheets

(56) References Cited

OTHER PUBLICATIONS

De Souza et al. "A Synergistic Effect of a Daily Supplement for 1 Month of 200 mg Magnesium plus 50 mg Vitamin B6 for the Relief of Anxiety-Related Premenstrual Symptoms: A Randomized, Double-Blind, Crossover Study." J Womens Health Gend Based Med. Mar. 2000; 9(2):131-9 published Mar. 9, 2000.
Fathizadeh et al. "Evaluating the effect of magnesium and magnesium plus vitamin B6 supplement on the severity of premenstrual syndrome." Iran J Nurs Midwifery Res. Dec. 2010; 15(Suppl1): 401-405. published Sep. 21, 2011.
Ivazzo et al. "Boric Acid for Recurrent Vulvovaginal Candidiasis: The Clinical Evidence" J Womens Health (Larchmt) Aug. 2011 ;20(8):1245-55 published Jul. 20, 2011.
Laith Alasadi "Vaginal Absorption." https://es.slideshare.net/laithalasadi/vaginal-absorption published Dec. 9, 2016.
Mirabi et al. "Effect of Medicinal Herbs on Primary Dysmenorrhoea-a Systematic Review" Iran J Pharm Res. 2014 Summer; 13(3): 757-767 published Summer 2014.
Ordikhani et al. "Drug Delivery Approaches for the Treatment of Cervical Cancer" Pharmaceutics Jul. 20, 2016;8(3):23 published Jul. 20, 2016.
Prashant Deore "Intrauterine Intravaginal Drug Delivery System" https://www.slideshare.net/PRASHANTDEORE1/intrauterine-intravaginal-drug-delivery-system date published Mar. 3, 2015.
Sun et al. "Efficacy of vitamin B complex as an adjuvant therapy for the treatment of complicated vulvovaginal candidiasis: An in vivo and in vitro study" Biomed Pharmacother Apr. 2017;88:770-777 published Jan. 31, 2017.

\* cited by examiner

COMPOSITIONS, DELIVERY DEVICES, AND METHODS THEREOF FOR FEMININE HEALTH

BACKGROUND

The use of feminine hygiene products is important in overall feminine health and hygiene. Feminine hygiene products are frequently used for least 5-7 days out of a month during menstruation when such feminine hygiene products are placed in the vagina or over the vulva to absorb menstrual fluids. Women can experience menstrual symptoms before, during, and after menstruation including painful abdominal cramping that can interfere with daily activities. Currently, the absorption of menstrual fluids and treating menstrual symptoms such as cramping or pain are treated as two separate events. For the absorption of menstrual fluids, women use feminine hygiene products such as tampons, sanitary napkins, or menstrual cups. For treating menstrual symptoms, women often use remedies such as oral pain medications or heating pads applied to affected areas. However, there are a lack of options that combine the ability to absorb menstrual fluids while treating menstrual symptoms before, during, and after menstruation.

As such, provided herein are compositions, delivery devices, and methods thereof for feminine health.

SUMMARY

Disclosed herein is a composition for feminine health including, in some embodiments, a continuous phase and a dispersed phase dispersed throughout the continuous phase forming a fluid suspension. The continuous phase includes a solvent of one or more essential oils, one or more lubricants, or a combination thereof. The continuous phase also includes one or more solutes dissolved in the solvent. The one or more solutes include one or more fat-soluble vitamins. The dispersed phase includes a pH-balancing agent, a dietary mineral, an absorbent, one or more water-soluble vitamins, or a combination thereof. The suspension is configured for absorption by an absorbent substrate of a feminine hygiene product.

In some embodiments, the composition includes the dietary mineral and the one or more water-soluble vitamins. The dietary mineral includes magnesium. The one or more water-soluble vitamins include vitamin $B_6$ and folic acid.

In some embodiments, the composition includes the one or more essential oils. The one or more essential oils are selected from thuja oil, tea tree oil, calendula oil, and comfrey oil.

In some embodiments, the composition includes the one or more lubricants. The one or more lubricants are selected from coconut oil, aloe vera, and olive oil.

In some embodiments, the composition includes the one or more fat-soluble vitamins. The one or more fat-soluble vitamins are selected from vitamin A and vitamin E.

In some embodiments the composition includes the pH-balancing agent. The pH-balancing agent includes boric acid.

In some embodiments, the composition includes the dietary mineral. The dietary mineral includes magnesium.

In some embodiments, the composition includes the absorbent. The absorbent includes charcoal.

In some embodiments, the composition includes one or more water-soluble vitamins. The one or more water-soluble vitamins are selected from vitamin $B_6$ and folic acid.

In some embodiments, the composition includes the continuous phase as the one or more solutes dissolved in the solvent as the combination of the one or more essential oils and the one or more lubricants. The composition also includes the dispersed phase as the combination of the pH-balancing agent, the dietary mineral, the absorbent, and the one or more water-soluble vitamins.

In some embodiments, the one or more essential oils are selected from thuja oil, tea tree oil, calendula oil, and comfrey oil; the one or more lubricants are selected from coconut oil, aloe vera, and olive oil; the one or more fat-soluble vitamins are selected from vitamin A and vitamin E; the pH-balancing agent includes boric acid; the dietary mineral includes magnesium; the absorbent includes charcoal; and the one or more water-soluble vitamins are selected from vitamin $B_6$ and folic acid.

Also disclosed herein is a delivery device for feminine health including, in some embodiments, a feminine hygiene product including an absorbent substrate and a composition absorbed onto the absorbent substrate. The feminine hygiene product is configured to be placed against a vulva, inserted into a vagina, or both. The composition includes a continuous phase and a dispersed phase dispersed throughout the continuous phase forming a fluid suspension. The continuous phase includes a solvent of one or more essential oils, one or more lubricants, or a combination thereof. The continuous phase also includes one or more solutes dissolved in the solvent. The one or more solutes include one or more fat-soluble vitamins. The dispersed phase includes a pH-balancing agent, a dietary mineral, an absorbent, one or more water-soluble vitamins, or a combination thereof. The dispersed phase is dispersed throughout the continuous phase forming a fluid suspension configured for absorption by the absorbent substrate of the feminine hygiene product.

In some embodiments, the feminine hygiene product includes a sanitary napkin.

In some embodiments, the feminine hygiene product includes a tampon.

In some embodiments, the composition includes the dietary mineral and the one or more water-soluble vitamins. The dietary mineral includes magnesium. The one or more water-soluble vitamins include vitamin $B_6$ and folic acid.

In some embodiments, the composition includes the one or more essential oils. The one or more essential oils are selected from thuja oil, tea tree oil, calendula oil, and comfrey oil.

In some embodiments, the composition includes the one or more lubricants. The one or more lubricants are selected from coconut oil, aloe vera, and olive oil.

In some embodiments, the composition includes the one or more fat-soluble vitamins. The one or more fat-soluble vitamins are selected from vitamin A and vitamin E.

In some embodiments, the composition includes the pH-balancing agent. The pH-balancing agent includes boric acid.

In some embodiments, the composition includes the dietary mineral. The dietary mineral includes magnesium.

In some embodiments, the composition includes the absorbent. The absorbent includes charcoal.

In some embodiments, the composition includes the one or more water-soluble vitamins. The one or more water-soluble vitamins are selected from vitamin $B_6$ and folic acid.

In some embodiments, the composition includes the continuous phase as the one or more solutes dissolved in the solvent as the combination of the one or more essential oils and the one or more lubricants. The composition also includes the dispersed phase as the combination of the pH-balancing agent, the dietary mineral, the absorbent, and the one or more water-soluble vitamins.

In some embodiments, the one or more essential oils are selected from thuja oil, tea tree oil, calendula oil, and comfrey oil; the one or more lubricants are selected from coconut oil, aloe vera, and olive oil; the one or more fat-soluble vitamins are selected from vitamin A and vitamin E; the pH-balancing agent includes boric acid; the dietary mineral includes magnesium; the absorbent includes charcoal; and the one or more water-soluble vitamins are selected from vitamin $B_6$ and folic acid.

Also disclosed herein is a delivery device for feminine health including, in some embodiments, a feminine hygiene product including an absorbent substrate and a composition absorbed onto the absorbent substrate. The feminine hygiene product is configured to be placed against a vulva, inserted into a vagina, or both. The composition includes a probiotic of the genus *Lactobacillus*.

Also disclosed herein is a method of making a delivery device for feminine health including, in some embodiments, an obtaining step of obtaining a feminine hygiene product, a preparing step of preparing a composition for feminine health, a filling step of filling a dispensing device with the composition, and a dispensing step of dispensing the composition onto an absorbent substrate of the feminine hygiene product using the dispensing device, thereby forming the delivery device. The preparing step includes a dissolving step and a dispersing step. The dissolving step includes dissolving one or more solutes of the composition in a solvent of one or more essential oils, one or more lubricants, or a combination thereof to form a solution for a continuous phase. The dispersing step includes dispersing particles of a pH-balancing agent, a dietary mineral, an absorbent, one or more water-soluble vitamins, or a combination thereof in the continuous phase to form a dispersed phase in the continuous phase, thereby forming a fluid suspension.

In some embodiments, the dispensing step includes spraying the composition onto the absorbent substrate of the feminine hygiene product.

In some embodiments, the dispensing step includes injecting the composition into the absorbent substrate of the feminine hygiene product.

In some embodiments, the method further includes a packaging step of packaging the delivery device including the composition on the absorbent substrate thereof into a single-use package.

In some embodiments, the feminine hygiene product is a sanitary napkin.

In some embodiments, the feminine hygiene product is a tampon.

Also disclosed herein is a method for feminine health including, in some embodiments, an obtaining step of obtaining a delivery device including a composition for feminine health, an applying step of applying the delivery device, and a removing step of removing the delivery device. The composition includes a continuous phase and a dispersed phase in the continuous phase. The continuous phase is a solution of one or more solutes dissolved in a solvent of one or more essential oils, one or more lubricants, or a combination thereof. The dispersed phase is particles of a pH-balancing agent, a dietary mineral, an absorbent, one or more water-soluble vitamins, or a combination thereof. The applying step includes applying the delivery device to a vulva, inserting the delivery device into a vagina, or a combination thereof. The removing step includes removing the delivery device after a period of time.

In some embodiments, the composition includes the dietary mineral and the one or more water-soluble vitamins. The dietary mineral includes magnesium. The one or more water-soluble vitamins include vitamin $B_6$ and folic acid.

In some embodiments, the composition includes the pH-balancing agent. The pH-balancing agent includes boric acid.

In some embodiments, the composition includes the one or more essential oils. The one or more essential oils include calendula oil.

In some embodiments, the method further includes an un-packaging step including removing the delivery device from a single-use package including the delivery device.

In some embodiments, the feminine hygiene product is a sanitary napkin.

In some embodiments, the feminine hygiene product is a tampon.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

As set forth above, there are a lack of options that combine the ability to absorb menstrual fluids while treating menstrual symptoms before, during, and after menstruation. As such, provided herein are compositions, delivery devices, and methods thereof for feminine health.

Delivery Devices

Figure 2:
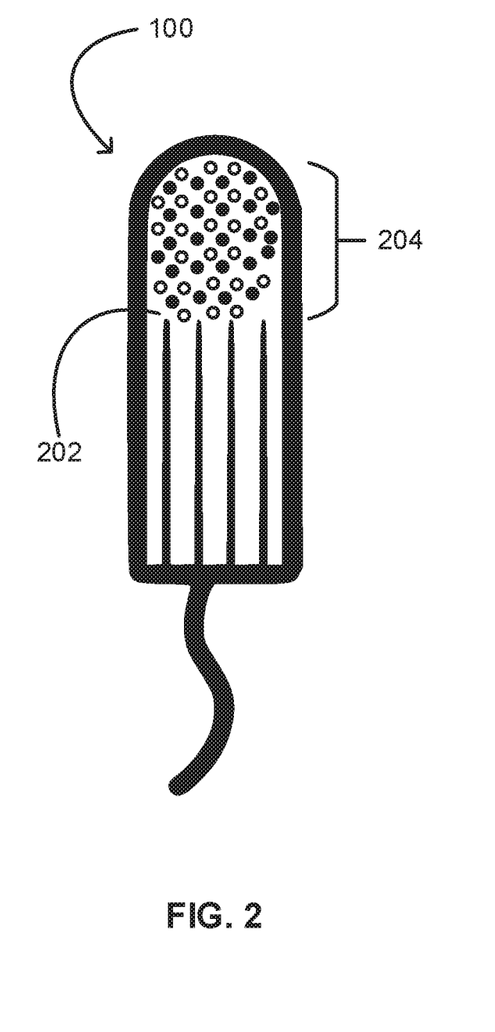
FIG. 2 illustrates a first delivery device for feminine health in accordance with some embodiments.
Figure 3:
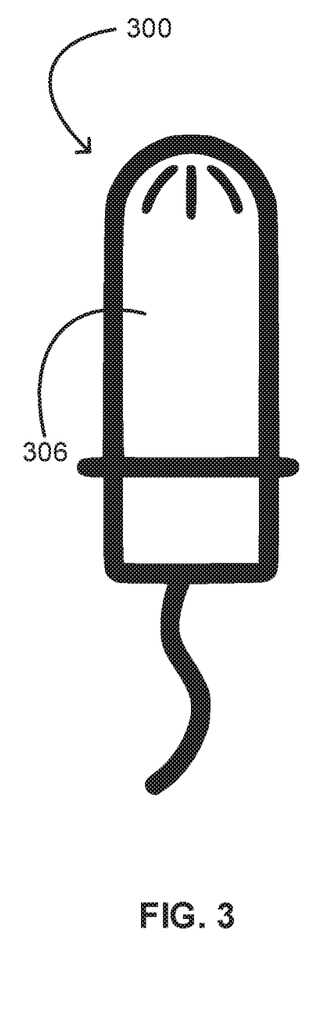
FIG. 3 illustrates an applicator of the first delivery in accordance with some embodiments.
Figure 10:
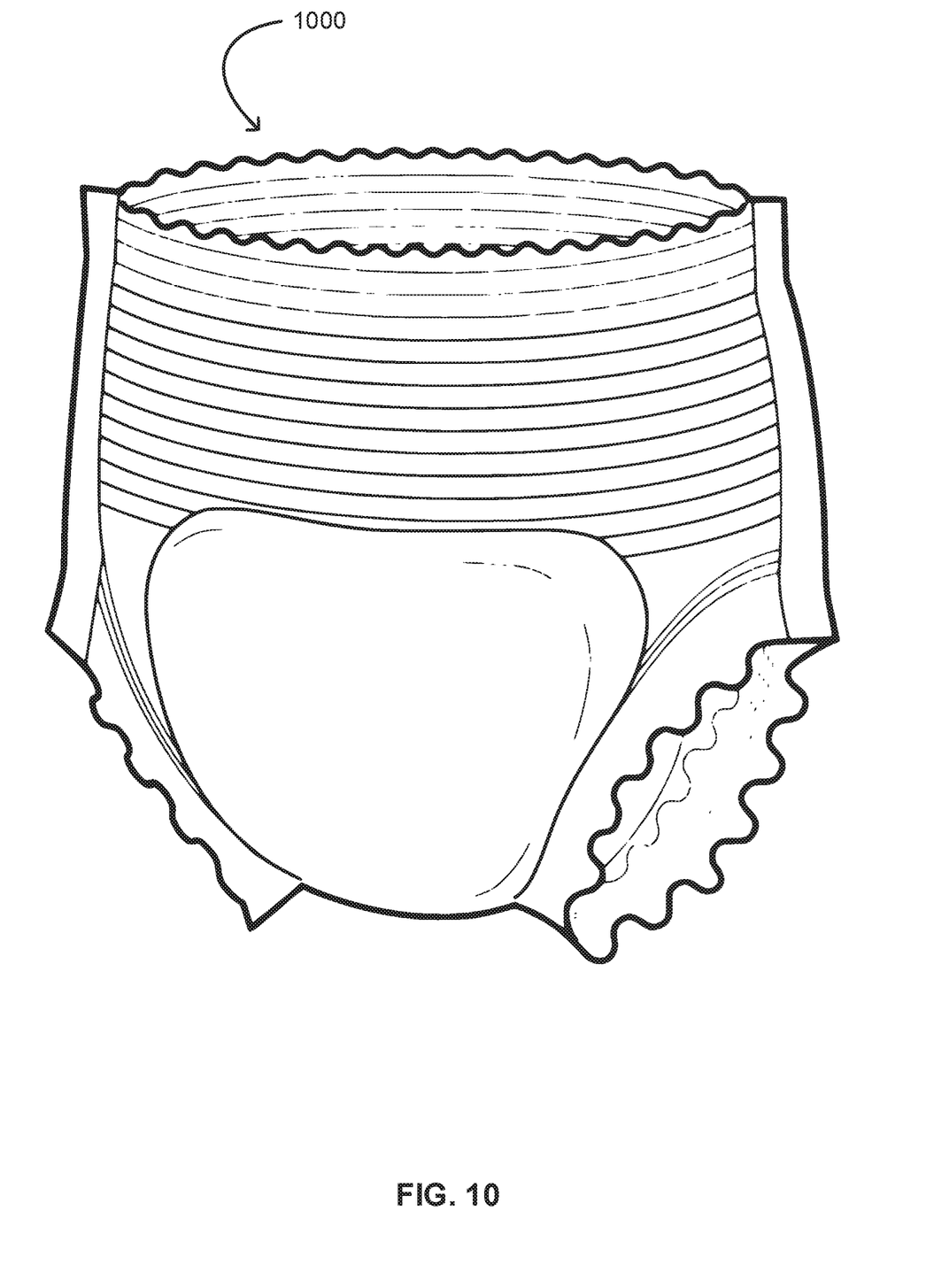
FIG. 10 illustrates a seventh delivery device for feminine health in accordance with some embodiments.

FIG. 2 illustrates a delivery device 100 for feminine health in accordance with some embodiments. FIGS. 5-9 illustrates delivery devices 500, 600, 700, 800, and 900 for feminine health in accordance with some embodiments. FIG. 10 illustrates a delivery device 1000 for feminine health in accordance with some embodiments.

As shown, the delivery devices 100, 500, 600, 700, 800, 900, and 1000 include feminine hygiene products, or the like, including absorbent substrates and a composition 204 absorbed onto the absorbent substrates.

Figure 1:
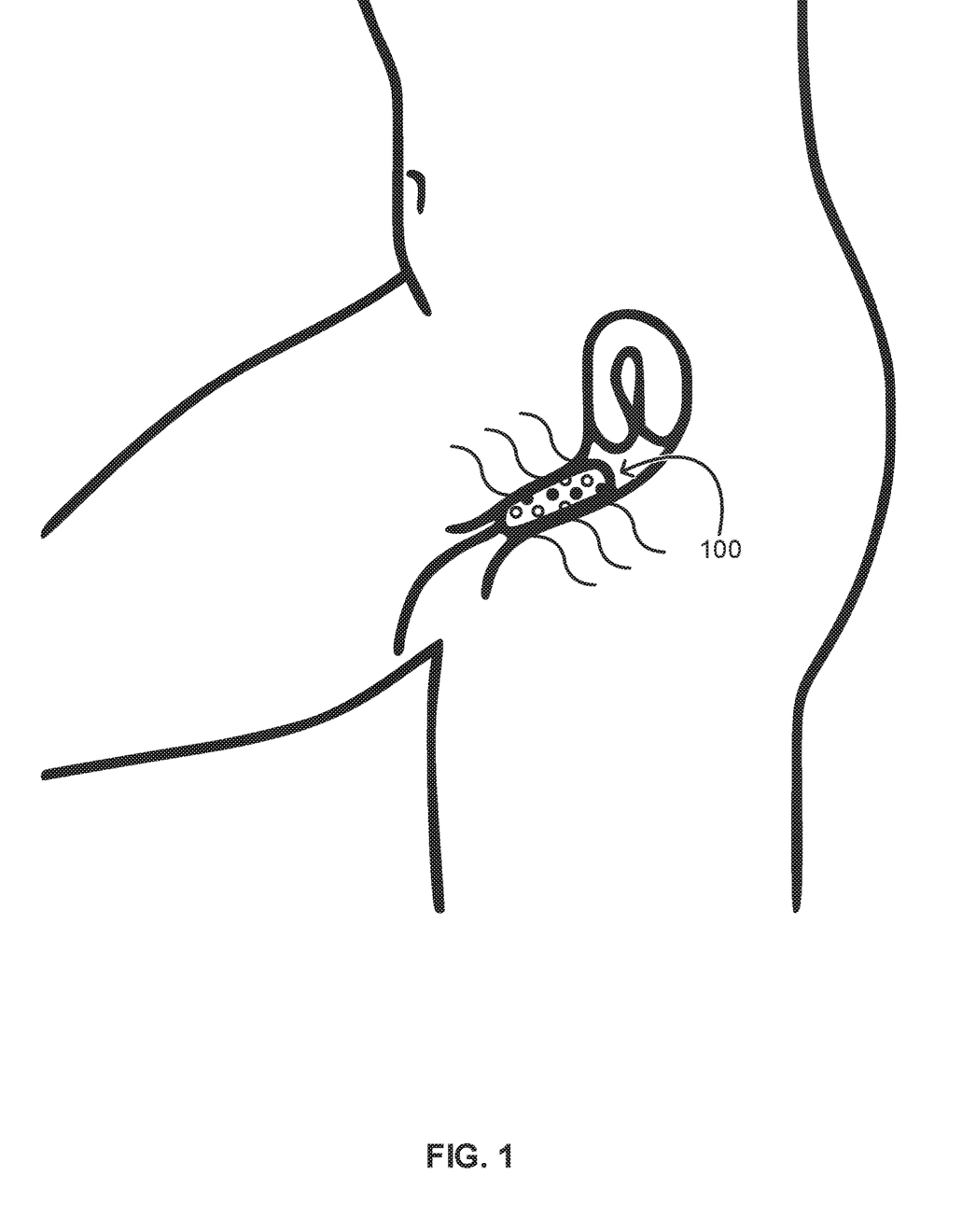
FIG. 1 illustrates use of a delivery device for feminine health in accordance with some embodiments.

The delivery device 100 is a tampon configured for placement in a vagina, which is ideal for its high vascularization and rapid absorption of the composition 204 as shown in FIG. 1. The delivery device includes an absorbent substrate 202 and the composition 204 absorbed onto the absorbent substrate 202. The delivery device 100 can include an applicator 306 (e.g., plastic, cardboard, etc.) configured to facilitate insertion of the delivery device 100 into the vagina. The delivery device 100 can be packaged with packaging 408 into a single-use package 408.

The delivery device 500, 600, 700, 800, or 900, is a sanitary napkin configured for placement over a vulva. The delivery device 500, 600, 700, 800, or 900 includes an absorbent substrate 502, 602, 702, 802, or 902 and the composition 204 absorbed onto the absorbent substrate 502, 602, 702, 802, or 902. Similarly, delivery devices can also include incontinence pads with the composition 204 absorbed onto the absorbent substrates thereof. Like the delivery device 100, the delivery 500, 600, 700, 800, or 900 can be packaged with packaging into a single-use package.

The delivery device 1000 is an adult diaper. While not shown, the delivery device 1000 includes an absorbent substrate and the composition 204 absorbed onto the absorbent substrate. The delivery device 1000 is configured to be worn with a least a portion of the absorbent substrate over the vulva. Like the delivery device 100, the delivery 1000 can be packaged with packaging into a single-use package.

The delivery devices for feminine health are not limited to the delivery devices 100, 500, 600, 700, 800, 900, and 1000. Indeed, different combinations of the delivery devices 100, 500, 600, 700, 800, 900, and 1000 are possible. For example, the delivery device 100 and any delivery device of the delivery devices 500, 600, 700, 800, 900, and 1000 can be combined into an integral delivery device for feminine health. In addition, two or more delivery devices of the delivery devices 100, 500, 600, 700, 800, 900, and 1000 can be used in combination as set forth below.

Each absorbent substrate of the absorbent substrate 202 of the delivery device 100, the absorbent substrate 502, 602, 702, 802, or 902 of the delivery device 500, 600, 700, 800, or 900, and the absorbent substrate of the delivery device 1000 can include a natural material (e.g., a natural fiber), a synthetic material (e.g., a synthetic fiber), or a blend thereof for the absorbent substrate. For example, the absorbent substrate 202, the absorbent substrate 502, 602, 702, 802, or 902, or the absorbent substrate of the delivery device 1000 can be cotton. The absorbent substrate 202, the absorbent substrate 502, 602, 702, 802, or 902, or the absorbent substrate of the delivery device 1000 can be rayon or polyester. The absorbent substrate 202, the absorbent substrate 502, 602, 702, 802, or 902, or the absorbent substrate of the delivery device 1000 can be a blend of cotton and rayon. Optionally, the absorbent substrate 202, the absorbent substrate 502, 602, 702, 802, or 902, or the absorbent substrate of the delivery device 1000 can further include one or more superabsorbent polymers.

Each type of delivery device of the delivery devices 100, 500, 600, 700, 800, 900, and 1000 can be configured to have one of more different absorbencies, which, in turn, is useful for providing one or more different doses of the composition 204. Different doses of the composition 204 are useful for treating different menstrual symptoms or menstrual symptoms of varying severity. Such doses are set forth below.

Advantageously, the delivery devices 100, 500, 600, 700, 800, 900, and 1000, particularly the delivery device 100, can be used over longer courses than similar products lacking the composition 204. Indeed, the delivery device 100 is configured to be used up to twice as long as a tampon in accordance with different embodiments of the composition 204. In addition, the delivery device 100 can be configured for one or more courses of treatment before, during, or after menstruation or even in no relation to menstruation at all. In one example, the delivery device 100 includes the enriching embodiment of the composition 204 for days of active menstruation (e.g., 3-5 days), the pH-balancing embodiment of the composition 204 for days immediately following the days of active menstruation (e.g., 2-3 days), or the revitalizing embodiment of the composition 204 for days following thereafter (e.g., 2-3 days). In another example, the delivery device 100 includes the coitus-enhancing embodiment of the composition 204 for days of active coitus (e.g., 2 days) or the post-coitus embodiment of the composition 204 for days immediately following the days of active coitus. In yet another example, the delivery device 100 includes a mature embodiment of the composition 204 for as-needed days (e.g., 2-5 days) to remedy menopausal symptoms or consequences thereof.

Compositions

The composition 204 includes, in some embodiments, a continuous phase and a dispersed phase dispersed throughout the continuous phase forming a fluid suspension. The composition 204 is configured for direct application or absorption by an absorbent substrate (e.g., the absorbent substrate 202, 502, 602, 702, 802, or 902) of a feminine hygiene product (e.g., a tampon or sanitary napkin), an incontinence product, or the like for application of the composition 204 therewith. However, the composition 204 is not limited to the suspension. For example, the composition 204 can include the continuous phase or the dispersed phase set forth below with the appreciation the continuous phase in the absence of the dispersed phase is the solvent or solution and the dispersed phase in the absence of the continuous phase is the pH-balancing agent, the dietary mineral, the absorbent, the one or more water-soluble vitamins, or the combination thereof. The one or more fat-soluble vitamins can be used independently or in combination with any one or more of the pH-balancing agent, the dietary mineral, the absorbent, or the one or more water-soluble vitamins.

The continuous phase includes a solvent of one or more essential oils, one or more lubricants, or a combination thereof. The continuous phase can include one or more solutes dissolved in the solvent, thereby forming a solution. The one or more solutes can include one or more fat-soluble vitamins, but the one or more solutes are not limited thereto.

The dispersed phase includes a pH-balancing agent, a dietary mineral, an absorbent, one or more water-soluble vitamins, a probiotic, or a combination thereof.

The one or more essential oils in the composition 204 can include, but are not limited to, calendula oil, thuja oil, tea tree oil, comfrey oil, chamomile oil, or a combination thereof. Essential oils have been demonstrated to reduce and relieve pain and other menstrual symptoms. For example, it has been demonstrated that calendula oil reduces pain associated with menstrual cramping by shortening the axons of nerve cells in the uterus, thereby reducing pain signals along these axons to the brain. *Thuja* oil is thought to help relieve menstrual cramping, bloating, and mood swings by acting as an emmenagogue. Tea tree oil is a source of terpenes and terpenoids, of which at least terpinen-4-ol has an antibacterial and antifungal effect. Comfrey oil has been demonstrated to reduce pain and swelling. Comfrey oil is also used in naturopathy as vaginal lubricant.

With respect to the one or more essential oils in the composition 204, the composition 204 can individually or collectively include at least about 1%, 10%, 20%, 30%, 40%, 50%, 60%, 70%, 80%, 90%, or 99%, or an intervening concentration thereof, of the one or more essential oils by weight of the composition 204. The composition 204 can individually or collectively include no more than about 99%, 90%, 80%, 70%, 60%, 50%, 40%, 30%, 20%, 10%, or 1%, or an intervening concentration thereof, of the one or more essential oils by weight of the composition 204. As such, the composition 204 can individually or collectively include the one or more essential oils in a concentration range of at least about 1% and no more than about 99% of the one or more essential oils by weight of the composition 204, including at least about 10% and no more than about 90% of the one or more essential oils by weight of the composition 204, such as at least about 20% and no more than about 80% of the one or more essential oils by weight of the composition 204, for example, at least about 30% and no more than about 70% of the one or more essential oils by weight of the composition 204. The individual or collective concentration of the one or more essential oils in the composition 204 can be increased or reduced as needed for optimization of feminine health.

The one or more lubricants in the composition 204 can include, but are not limited to, coconut oil, aloe vera, olive oil, or a combination thereof. Lubricants such as coconut oil, aloe vera, and olive oil are effective naturally occurring lubricants, which provide moisture to enhance comfort while donning a delivery device set forth herein.

With respect to the one or more lubricants in the composition 204, the composition 204 can individually or collectively include at least about 1%, 10%, 20%, 30%, 40%, 50%, 60%, 70%, 80%, 90%, or 99%, or an intervening concentration thereof, of the one or more lubricants by weight of the composition 204. The composition 204 can individually or collectively include no more than about 99%, 90%, 80%, 70%, 60%, 50%, 40%, 30%, 20%, 10%, or 1%, or an intervening concentration thereof, of the one or more lubricants by weight of the composition 204. As such, the composition 204 can individually or collectively include the one or more lubricants in a concentration range of at least about 1% and no more than about 99% of the one or more lubricants by weight of the composition 204, including at least about 10% and no more than about 90% of the one or more lubricants by weight of the composition 204, such as at least about 20% and no more than about 80% of the one or more lubricants by weight of the composition 204, for example, at least about 30% and no more than about 70% of the one or more lubricants by weight of the composition 204. The individual or collective concentration of the one or more lubricants in the composition 204 can be increased or reduced as needed for optimization of feminine health.

The one or more fat-soluble vitamins in the composition 204 can include, but are not limited to, vitamin A, vitamin E, or a combination thereof. The one or more fat-soluble vitamins can include one of more forms thereof. For example, vitamin A can be in a form selected from retinol, retinal, and retinoic acid. In another example, vitamin E can be in a form selected from any of the four tocopherols (e.g., alpha-tocopherol) and four tocotrienols thereof. Fat-soluble vitamins such as vitamin A and vitamin E have been demonstrated to reduce vaginal drying and increase soothing of the vaginal lining. Vitamin A has been demonstrated to be essential for female reproduction.

With respect to the one or more fat-soluble vitamins in the composition 204, the composition 204 can individually or collectively include at least about 1%, 10%, 20%, 30%, 40%, 50%, 60%, 70%, 80%, 90%, or 99%, or an intervening concentration thereof, of the one or more fat-soluble vitamins by weight of the composition 204. The composition 204 can individually or collectively include no more than about 99%, 90%, 80%, 70%, 60%, 50%, 40%, 30%, 20%, 10%, or 1%, or an intervening concentration thereof, of the one or more fat-soluble vitamins by weight of the composition 204. As such, the composition 204 can individually or collectively include the one or more fat-soluble vitamins in a concentration range of at least about 1% and no more than about 99% of the one or more fat-soluble vitamins by weight of the composition 204, including at least about 10% and no more than about 90% of the one or more fat-soluble vitamins by weight of the composition 204, such as at least about 20% and no more than about 80% of the one or more fat-soluble vitamins by weight of the composition 204, for example, at least about 30% and no more than about 70% of the one or more fat-soluble vitamins by weight of the composition 204. The individual or collective concentration of the one or more fat-soluble vitamins in the composition 204 can be increased or reduced as needed for optimization of feminine health.

The one or more water-soluble vitamins in the composition 204 can include, but are not limited to, B vitamins such as vitamin $B_1$ (i.e., thiamine), vitamin $B_2$ (i.e., riboflavin), vitamin $B_3$ (e.g., niacin, nicotinamide, or nicotinamide riboside), vitamin $B_5$ (i.e., pantothenic acid), vitamin $B_6$ (e.g., pyridoxine, pyridoxyl, or pyridoxamine), vitamin $B_7$ (i.e., biotin), vitamin $B_9$ (e.g., folic acid or folate), or vitamin $B_{12}$ (e.g., various cobalamins such as cyanocobalamin or methylcobalamin). Water-soluble vitamins such as vitamin $B_6$ and vitamin $B_9$ have been demonstrated to reduce fungal infections caused by the species of the genus *Candida* in mouse models and humans patients suffering from bacterial vaginitis. Furthermore, vitamin $B_6$ supplementation has been demonstrated to provide some relief of anxiety-related menstrual symptoms.

With respect to the one or more water-soluble vitamins in the composition 204, the composition 204 can individually or collectively include at least about 1%, 10%, 20%, 30%, 40%, 50%, 60%, 70%, 80%, 90%, or 99%, or an intervening concentration thereof, of the one or more water-soluble vitamins by weight of the composition 204. The composition 204 can individually or collectively include no more than about 99%, 90%, 80%, 70%, 60%, 50%, 40%, 30%, 20%, 10%, or 1%, or an intervening concentration thereof, of the one or more water-soluble vitamins by weight of the composition 204. As such, the composition 204 can individually or collectively include the one or more water-soluble vitamins in a concentration range of at least about 1% and no more than about 99% of the one or more water-soluble vitamins by weight of the composition 204, including at least about 10% and no more than about 90% of the one or more water-soluble vitamins by weight of the composition 204, such as at least about 20% and no more than about 80% of the one or more water-soluble vitamins by weight of the composition 204, for example, at least about 30% and no more than about 70% of the one or more water-soluble vitamins by weight of the composition 204. The individual or collective concentration of the one or more water-soluble vitamins in the composition 204 can be increased or reduced as needed for optimization of feminine health.

The dietary mineral in the composition 204 can include, but is not limited to, dietary magnesium. For example, the dietary magnesium can include magnesium citrate, magnesium oxide, magnesium chloride, magnesium lactate, magnesium aspartate, or magnesium sulfate. Dietary magnesium with vitamin $B_6$ supplementation has been demonstrated to reduce menstrual symptoms of depression and anxiety greater than magnesium alone or placebo.

With respect to the dietary mineral in the composition 204, the composition 204 can include at least about 1%, 10%, 20%, 30%, 40%, 50%, 60%, 70%, 80%, 90%, or 99%, or an intervening concentration thereof, of the dietary mineral by weight of the composition 204. The composition 204 can include no more than about 99%, 90%, 80%, 70%, 60%, 50%, 40%, 30%, 20%, 10%, or 1%, or an intervening concentration thereof, of the dietary mineral by weight of the composition 204. As such, the composition 204 can include the dietary mineral in a concentration range of at least about 1% and no more than about 99% of the dietary mineral by weight of the composition 204, including at least about 10% and no more than about 90% of the dietary mineral by weight of the composition 204, such as at least about 20% and no more than about 80% of the dietary mineral by weight of the composition 204, for example, at least about 30% and no more than about 70% of the dietary mineral by weight of the composition 204. The concentration of the dietary mineral in the composition 204 can be increased or reduced as needed for optimization of feminine health.

The pH-balancing agent in the composition 204 can include, but is not limited to, boric acid. Boric acid has been demonstrated to not only balance vaginal flora, but boric acid can help maintain a low pH through its ability to be a weak acid. Maintaining a mildly acidic pH in the vagina is crucial for the resistance to yeast infections, bacterial vaginosis, and *trichomonas*.

With respect to the pH-balancing agent in the composition 204, the composition 204 can include at least about 1%, 10%, 20%, 30%, 40%, 50%, 60%, 70%, 80%, 90%, or 99%, or an intervening concentration thereof, of the pH-balancing agent by weight of the composition 204. The composition 204 can include no more than about 99%, 90%, 80%, 70%, 60%, 50%, 40%, 30%, 20%, 10%, or 1%, or an intervening concentration thereof, of the pH-balancing agent by weight of the composition 204. As such, the composition 204 can include the pH-balancing agent in a concentration range of at least about 1% and no more than about 99% of the pH-balancing agent by weight of the composition 204, including at least about 10% and no more than about 90% of the pH-balancing agent by weight of the composition 204, such as at least about 20% and no more than about 80% of the pH-balancing agent by weight of the composition 204, for example, at least about 30% and no more than about 70% of the pH-balancing agent by weight of the composition 204. The concentration of the pH-balancing agent in the composition 204 can be increased or reduced as needed for optimization of feminine health.

The probiotic in the composition 204 can include, but is not limited to, bacteria in the genus *Lactobacillus* such as *L. acidophilus* and *L. rhamnosus*. A majority of the bacteria in the vagina of a majority of healthy females is of the genus *Lactobacillus*. In addition, it has been shown that $H_2O_2$-producing species such as *L. acidophilus* and *L. rhamnosus* can normalize vaginal pH and balance vaginal microbiota, thereby preventing or relieving bacterial vaginosis.

With respect to the probiotic in the composition 204, the composition 204 can include at least about 1%, 10%, 20%, 30%, 40%, 50%, 60%, 70%, 80%, 90%, or 99%, or an intervening concentration thereof, of the probiotic by weight of the composition 204. The composition 204 can include no more than about 99%, 90%, 80%, 70%, 60%, 50%, 40%, 30%, 20%, 10%, or 1%, or an intervening concentration thereof, of the probiotic by weight of the composition 204. As such, the composition 204 can include the probiotic in a concentration range of at least about 1% and no more than about 99% of the probiotic by weight of the composition 204, including at least about 10% and no more than about 90% of the probiotic by weight of the composition 204, such as at least about 20% and no more than about 80% of the probiotic by weight of the composition 204, for example, at least about 30% and no more than about 70% of the probiotic by weight of the composition 204. The concentration of the probiotic in the composition 204 can be increased or reduced as needed for optimization of feminine health.

The absorbent in the composition 204 can include, but is not limited to, charcoal such as activated charcoal. Activated charcoal is porous, allowing it to bind toxins and odors. Charcoal is not absorbed by the body, allowing for easy removal of toxins and odors from the body.

With respect to the absorbent in the composition 204, the composition 204 can include at least about 1%, 10%, 20%, 30%, 40%, 50%, 60%, 70%, 80%, 90%, or 99%, or an intervening concentration thereof, of the absorbent by weight of the composition 204. The composition 204 can include no more than about 99%, 90%, 80%, 70%, 60%, 50%, 40%, 30%, 20%, 10%, or 1%, or an intervening concentration thereof, of the absorbent by weight of the composition 204. As such, the composition 204 can include the absorbent in a concentration range of at least about 1% and no more than about 99% of the absorbent by weight of the composition 204, including at least about 10% and no more than about 90% of the absorbent by weight of the composition 204, such as at least about 20% and no more than about 80% of the absorbent by weight of the composition 204, for example, at least about 30% and no more than about 70% of the absorbent by weight of the composition 204. The concentration of the absorbent in the composition 204 can be increased or reduced as needed for optimization of feminine health.

The composition 204 can be configured to provide a protecting effect. In such embodiments, the composition 204 includes the dietary mineral, the one or more water-soluble vitamins, the pH-balancing agent, the absorbent, the one or more fat-soluble vitamins, and the one or more essential oils.

The dietary mineral includes magnesium. The one or more water-soluble vitamins include vitamin $B_6$ and folic acid. The pH-balancing agent includes boric acid. The absorbent includes charcoal. The one or more fat-soluble vitamins include vitamin A. The one or more essential oils include thuja oil and tea tree oil.

The composition 204 can be configured to provide a soothing effect. In such embodiments, the composition 204 includes the dietary mineral, the one or more water-soluble vitamins, the pH-balancing agent, the absorbent, the one or more fat-soluble vitamins, and the one or more essential oils. The dietary mineral includes magnesium. The one or more water-soluble vitamins include vitamin $B_6$ and folic acid. The pH-balancing agent includes boric acid. The absorbent includes charcoal. The one or more fat-soluble vitamins include vitamin E. The one or more essential oils include calendula oil and comfrey oil.

The composition 204 can be configured to provide a lubricating effect. In such embodiments, the composition 204 includes the dietary mineral, the one or more water-soluble vitamins, the pH-balancing agent, the absorbent, and the one or more lubricants. The dietary mineral includes magnesium. The one or more water-soluble vitamins include vitamin $B_6$ and folic acid. The pH-balancing agent includes boric acid. The absorbent includes charcoal. The one or more lubricants include coconut oil, aloe vera, or olive oil.

The composition 204 can be configured for one or more courses of treatment before, during, or after menstruation. For example, an enriching embodiment of the composition 204 for days of active menstruation (e.g., 3-5 days) can include magnesium as the dietary mineral and various B vitamins for the one or more water-soluble vitamins. A pH-balancing embodiment of the composition 204 for days immediately following the days of active menstruation (e.g., 2-3 days) can include a pH-balancing agent. A revitalizing embodiment of the composition 204 for days following thereafter (e.g., 2-3 days) can include calendula oil for the one or more essential oils.

The composition 204 can be configured for one or more courses of treatment in no relation to menstruation at all. For example, a coitus-enhancing embodiment of the composition 204 for days of active coitus (e.g., 2 days) can include coconut oil and aloe vera as the one or more lubricants and vitamin E for the one or more fat-soluble vitamins. A post-coitus embodiment of the composition 204 for days immediately following the days of active coitus can include thuja oil as the one or more essential oils and vitamin A for the one or more fat-soluble vitamins. A mature embodiment of the composition 204 for a number of as-needed days (e.g., 2-5 days) to remedy menopausal symptoms or consequences thereof can include comfrey oil and chamomile oil as the one or more essential oils.

Figure 4:
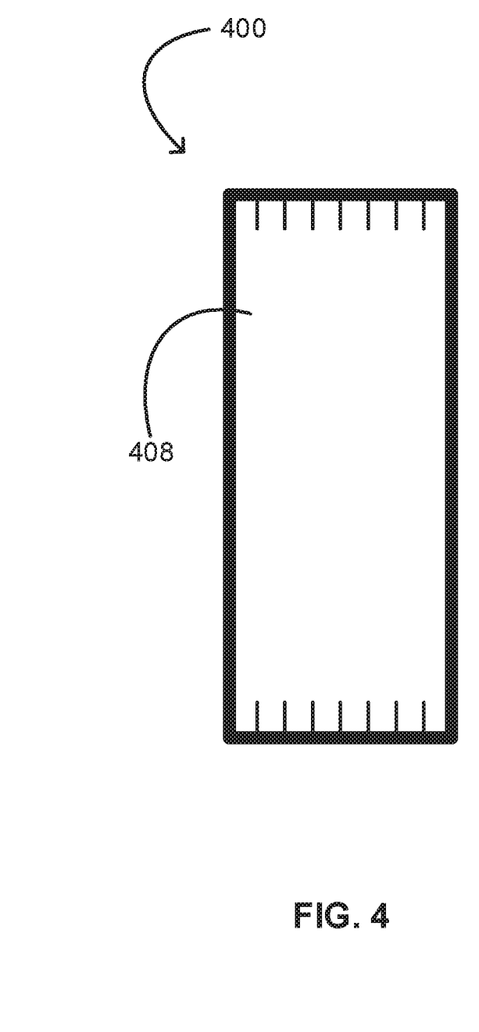
FIG. 4 illustrates a single-use package including the first delivery device in accordance with some embodiments.
Figure 5:
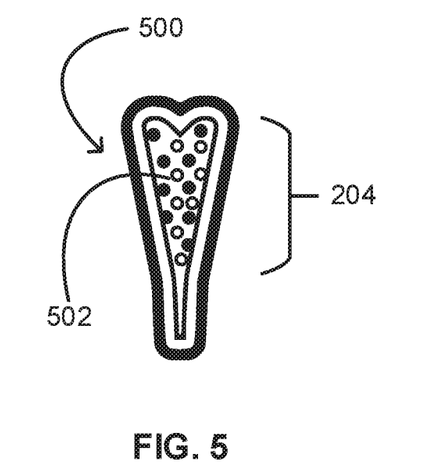
FIG. 5 illustrates a second delivery device for feminine health in accordance with some embodiments.
Figure 6:
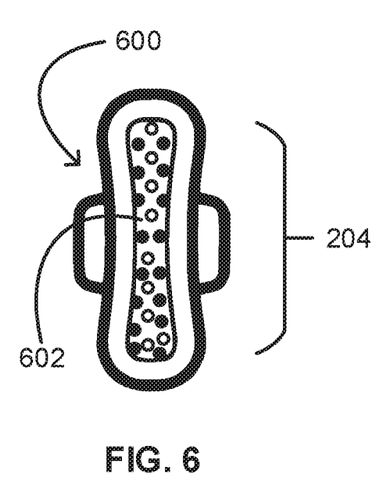
FIG. 6 illustrates a third delivery device for feminine health in accordance with some embodiments.
Figure 7:
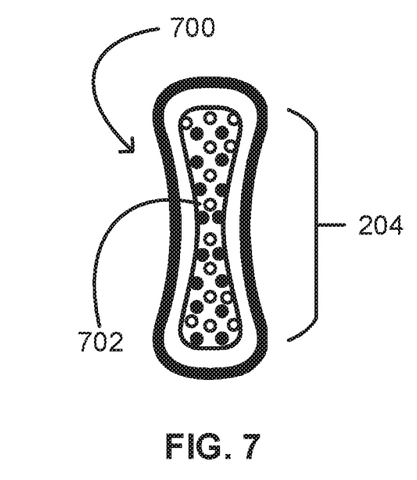
FIG. 7 illustrates a fourth delivery device for feminine health in accordance with some embodiments.
Figure 8:
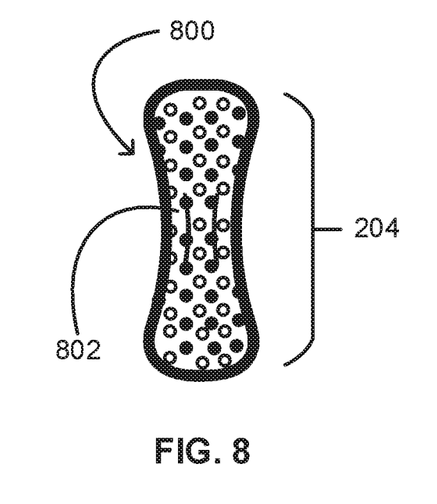
FIG. 8 illustrates a fifth delivery device for feminine health in accordance with some embodiments.
Figure 9:
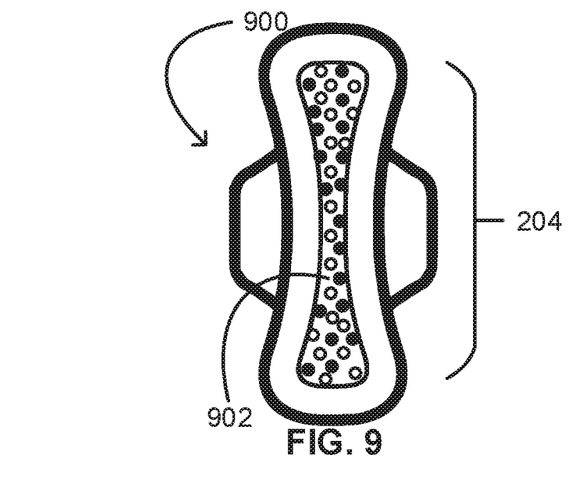
FIG. 9 illustrates a sixth delivery device for feminine health in accordance with some embodiments.

The composition 204 can be formulated into any administrable formulation that provides sufficient intravaginal or topical levels of the composition 204 upon administration of one or more doses of the formulation such as by direct application or by way of the delivery device 100, 500, 600, 700, 800, 900, or 1000. In addition to the composition 204, such a formulation can include any nutraceutically acceptable excipients needed for a multi-dose or single-dose dosage form suitable for at least intravaginal or topical administration. That said, the formulation need not include such excipients; that is, the formulation can be the composition 204, itself, in some embodiments. The multi-dose dosage form can be a bulk powder, paste, suspension, emulsion, or solution including the composition 204. The single-dose dosage form can be a pre-measured amount of the powder; a vaginal suppository; a pre-cut, vaginally disintegrating thin film; a pre-measured amount of the paste; or a pre-measured amount of the suspension, emulsion, or solution. The single-dose dosage form can be a pre-measured amount of the suspension, emulsion, or solution. For example, the composition 204 or the formulation including the composition 204 can be the suspension, which can be pre-measured and dispensed onto the absorbent substrate of a tampon and packaged into the single-use package 400 as a single dose for intravaginal administration.

With respect to doses, a single dose of the composition 204 or the formulation including the composition 204 can include at least about 0.001 g, 0.01 g, 0.1 g, 1 g, 2 g, 3 g, 4 g, 5 g, 6 g, 7 g, 8 g, 9 g, or 10 g, or an intervening amount (e.g., about 1.1 g, 1.2 g, 1.3 g, 1.4 g, 1.5 g, etc.) thereof, of the composition 204 or the formulation for an average sized woman. Alternatively, a single dose of the composition 204 or the formulation including the composition 204 can include no more than about 10 g, 9 g, 8 g, 7 g, 6 g, 5 g, 4 g, 3 g, 2 g, 1 g, 0.1 g, 0.001 g, 0.001 g, or an intervening amount (e.g., about 2.9 g, 2.8 g, 2.7 g, 2.6 g, 2.5 g, etc.) thereof, of the composition 204 or the formulation for an average sized woman. As such, a single dose of the composition 204 or the formulation including the composition 204 can include at least about 0.001 g and no more than about 10 g of the composition 204 or the formulation, which includes at least about 1 g and no more than about 8 g of the composition 204 or the formulation, such as at least about 2 g and no more than about 6 g of the composition 204 or the formulation, for example, at least about 2 g and no more than about 4 g of the composition 204 or the formulation. Different doses of the composition 204 or the formulation including the composition 204 are useful for at least treating different menstrual symptoms or menstrual symptoms of varying severity. As set forth above, each type of delivery device of the delivery devices 100, 500, 600, 700, 800, 900, and 1000 can be configured to have one of more different absorbencies, which, in turn, is useful for providing one or more of the foregoing doses of the composition 204 or the formulation including the composition 204.

Methods of Making Delivery Devices

Figure 11:
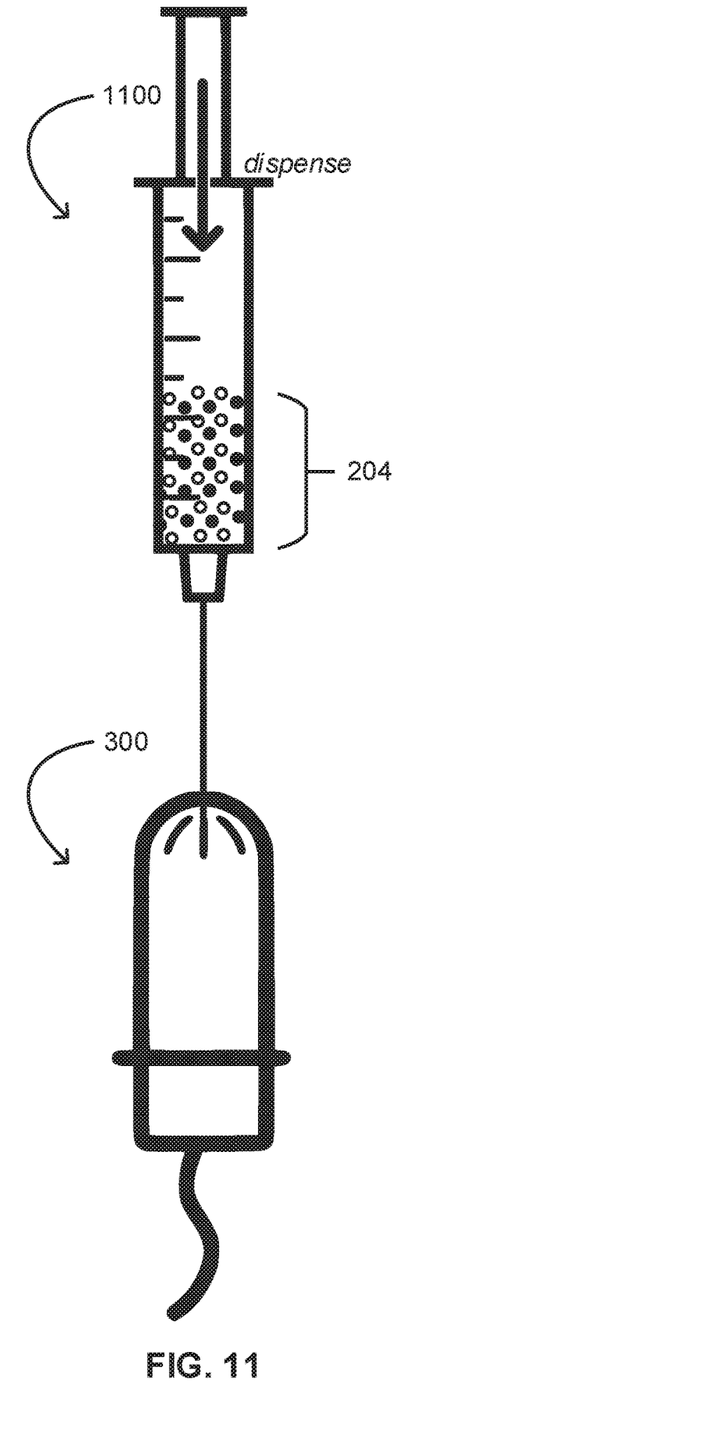
FIG. 11 illustrates a method of making the first delivery device in accordance with some embodiments.

FIG. 11 illustrates a portion of a method of making the delivery device 100 in accordance with some embodiments.

A method of making a delivery device (e.g., the delivery device 100, 500, 600, 700, 800, 900, or 1000) includes, in some embodiments, an obtaining step of obtaining a feminine hygiene product or the like (e.g., a tampon, a sanitary napkin, a diaper, etc.), a preparing step of preparing the composition 204 or a formulation including the composition 204, a filling step of filling a dispensing device (e.g., filling a barrel of a syringe 1100, filling a reservoir, optionally, of a sprayer, etc.) with the composition 204 of the formulation, and a dispensing step of dispensing the composition 204 or the formulation onto an absorbent substrate (e.g., the absorbent substrate 202, 502, 602, 702, 802, or 902) of the feminine hygiene product or the like using the dispensing device, thereby forming the delivery device.

The preparing step includes a dissolving step and a dispersing step. The dissolving step includes dissolving the one or more solutes of the composition 204 in a solvent of the one or more essential oils, the one or more lubricants, or a combination thereof to form a solution for the continuous phase. The dispersing step includes dispersing the particles of the pH-balancing agent, the dietary mineral, the absorbent, the one or more water-soluble vitamins, or a combination thereof in the continuous phase to form the dispersed phase in the continuous phase, thereby forming the fluid suspension configured for the filling step. During the dissolving step, the dispersing step, or a following step, excipients can be added to form the formulation including the composition 204.

The dispensing step includes injecting the composition 204 or the formulation including the composition 204 into the absorbent substrate of the feminine hygiene product or spraying the composition 204 or the formulation onto the absorbent substrate of the feminine hygiene product. In an alternative step to the dispensing step, the method of making the delivery device can include dipping, brushing, sponging, sprinkling, drizzling, or dusting the composition 204 or the formulation onto the absorbent substrate of the feminine hygiene product depending upon one or more physical characteristics of the composition 204 or the formulation. For example, the alternative step can include dipping the absorbent-substrate portion of the feminine hygiene product into a reservoir including the composition 204 or the formulation.

The method can further include a packaging step of packaging the delivery device including the composition 24 or the formulation including the composition 204 into a single-use package (e.g., the single-use package 400).

Methods of Using Delivery Devices

A method for feminine health includes, in some embodiments, an obtaining step of obtaining a delivery device (e.g., the delivery device 100, 500, 600, 700, 800, 900, or 1000) including the composition 204 or the formulation including the composition 204, an applying step of applying the delivery device, and a removing step of removing the delivery device.

The method can further include an un-packaging step including removing the delivery device (e.g., the delivery device 100) from a single-use package (e.g., the single-use package 400) including the delivery device.

The applying step includes inserting the delivery device into a vagina in the case of the delivery device 100, applying the delivery device to a vulva in the case of the delivery device 500, 600, 700, 800, 900, or 1000, or a combination thereof. As set forth above, the delivery device 100 and any delivery device of the delivery devices 500, 600, 700, 800, 900, and 1000 can be combined into an integral delivery device for feminine health, which integral delivery device is applied during the applying step by inserting the delivery device into the vagina, as well as applying the delivery device to the vulva. Alternatively, two or more delivery devices of the delivery devices 100, 500, 600, 700, 800, 900, and 1000 can be used in combination. For example, the delivery device 100 can be applied during the applying step by inserting the delivery device into the vagina, and the delivery device 500, 600, 700, 800, or 900 can be applied during the applying step by applying the delivery device 500, 600, 700, 800, or 900 to the vulva.

The removing step includes removing the delivery device after a period of time. The period of time can include at least about 2 hours, 3 hours, 4 hours, 5 hours, 6 hours, 7 hours, 8 hours, 9 hours, or 10 hours, or an intervening period of time (e.g., about 6.1 hours, 6.2 hours, 6.3 hours, 6.4 hours, 6.5 hours, etc.) thereof. The period of time can include no more than about 10 hours, 9 hours, 8 hours, 7 hours, 6 hours, 5 hours, 4 hours, 3 hours, or 2 hours, or an intervening period of time (e.g., about 7.9 hours, 7.8 hours, 7.7 hours, 7.6 hours, 7.5 hours, 7.4 hours, etc.) thereof. The period of time can include at least about 2 hours and no more than about 10 hours, which includes at least about 2 hours and no more than about 8 hours, such as at least about 4 hours and no more than about 8 hours, for example, at least about 4 hours and no more than about 6 hours. The period of time can be increased as desired or needed in accordance with a particular course of treatment.

The applying step followed by the removing step is typically repeated a number of times per day by a user. The applying step followed by the removing step can be repeated at least about 2, 3, 4, 5, 6, 7, 8, 9, 10, 11, or 12 times per day. The applying step followed by the removing step can be repeated no more than about 12, 11, 10, 9, 8, 7, 6, 5, 4, 3, or 2 times per day. The applying step followed by the removing step can be repeated at least about 2 times per day and no more than about 12 times per day, which includes at least about 2 times per day and no more than about 10 times per day, such as at least about 2 times per day and no more than about 8 times per day, for example, at least about 2 times per day and no more than about 6 times per day. The number of times per day the applying step followed by the removing step is typically repeated is in accordance with a prescribed course of treatment or a discretionary course of treatment.

As set forth above, a course of treatment can be before, during, or after menstruation or even in no relation to menstruation at all. The course of treatment can be at least about 1 day, 2 days, 3 days, 4 days, 5 days, 6 days, or 7 days, or an intervening number of days (e.g., about 2.1 days, 2.2 days, 2.3 days, 2.4 days, 2.5 days, etc.) thereof. The course of treatment can be no more than about 7 day, 6 days, 5 days, 4 days, 3 days, 2 days, or 1 day, or an intervening number of days (e.g., about 3.9 days, 3.8 days, 3.7 days, 3.6 days, 3.5 days, etc.) thereof. The course of treatment can be at least about 1 day and no more than about 7 days, which includes at least about 1 day and no more than about 5 days, such as at least about 1 day and no more than about 4 days, for example, at least about 1 day and no more than about 3 days. The number of days of the course of treatment can be increased or decreased as needed or desired in accordance with a practitioner's recommendation or the user's discretion.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A composition for feminine health, comprising:
   a continuous phase including:
      a solvent of one or more essential oils, one or more lubricants, or a combination thereof; and
      one or more solutes dissolved in the solvent including one or more fat-soluble vitamins; and
   a dispersed phase including a pH-balancing agent, a dietary mineral, an absorbent, one or more water-soluble vitamins, or a combination thereof, the dispersed phase dispersed throughout the continuous phase forming a fluid suspension configured for absorption by an absorbent substrate of a feminine hygiene product.

2. The composition of claim 1, wherein the composition includes the dietary mineral and the one or more water-soluble vitamins, the dietary mineral including magnesium and the one or more water-soluble vitamins including vitamin B6 and folic acid.

3. The composition of claim 1, wherein the composition includes the one or more essential oils, the one or more essential oils selected from thuja oil, tea tree oil, calendula oil, and comfrey oil.

4. The composition of claim 1, wherein the composition includes the one or more lubricants, the one or more lubricants selected from coconut oil, aloe vera, and olive oil.

5. The composition of claim 1, wherein the composition includes the one or more fat-soluble vitamins, the one or more fat-soluble vitamins selected from vitamin A and vitamin E.

6. The composition of claim 1, wherein the composition includes the pH-balancing agent, the pH-balancing agent including boric acid.

7. The composition of claim 1, wherein the composition includes the dietary mineral, the dietary mineral including magnesium.

8. The composition of claim 1, wherein the composition includes the absorbent, the absorbent including charcoal.

9. The composition of claim 1, wherein the composition includes the one or more water-soluble vitamins, the one or more water-soluble vitamins selected from vitamin B6 and folic acid.

10. The composition of claim 1, wherein the continuous phase is the one or more solutes dissolved in the solvent of the combination of the one or more essential oils and the one or more lubricants, and the dispersed phase is the combination of the pH-balancing agent, the dietary mineral, the absorbent, and the one or more water-soluble vitamins.

11. The composition of claim 10, wherein the one or more essential oils are selected from thuja oil, tea tree oil, calendula oil, and comfrey oil; the one or more lubricants are selected from coconut oil, aloe vera, and olive oil; the one or more fat-soluble vitamins are selected from vitamin A and vitamin E; the pH-balancing agent includes boric acid; the dietary mineral includes magnesium; the absorbent includes charcoal; and the one or more water-soluble vitamins are selected from vitamin B6 and folic acid.

12. The composition of claim 10, wherein the composition is configured for administration by way of placement of the feminine hygiene product against a vulva or insertion of the feminine hygiene product into a vagina.

13. A composition for feminine health, comprising:
a continuous phase including one or more fat-soluble vitamins dissolved in a combination of one or more essential oils and one or more lubricants; and
a dispersed phase including a pH-balancing agent, a dietary mineral, an absorbent, and one or more water-soluble vitamins, the dispersed phase dispersed throughout the continuous phase forming a fluid suspension configured for absorption by an absorbent substrate of a feminine hygiene product.

14. The composition of claim 13, wherein the one or more essential oils are selected from thuja oil, tea tree oil, calendula oil, and comfrey oil; the one or more lubricants are selected from coconut oil, aloe vera, and olive oil; the one or more fat-soluble vitamins are selected from vitamin A and vitamin E; the pH-balancing agent includes boric acid; the dietary mineral includes magnesium; the absorbent includes charcoal; and the one or more water-soluble vitamins are selected from vitamin B6 and folic acid.

15. A composition for feminine health, comprising:
a continuous phase including one or more fat-soluble vitamins selected from vitamin A and vitamin E dissolved in a combination of one or more essential oils and one or more lubricants, the one or more essential oils selected from thuja oil, tea tree oil, calendula oil, and comfrey oil with the one or more essential oils including at least thuja oil, calendula oil, or comfrey oil, and the one or more lubricants selected from coconut oil, aloe vera, and olive oil with the one or more lubricants including at least olive oil; and
a dispersed phase including boric acid as a pH-balancing agent, magnesium as a dietary mineral, charcoal as an absorbent, and one or more water-soluble vitamins selected from vitamin B6 and folic acid, the dispersed phase dispersed throughout the continuous phase forming a fluid suspension configured for absorption by an absorbent substrate of a feminine hygiene product.

16. The composition of claim 15, wherein the composition is configured for administration by way of placement of the feminine hygiene product against a vulva or insertion of the feminine hygiene product into a vagina.

* * * * *